(12) United States Patent  (10) Patent No.: US 9,036,970 B2
Guyon et al.  (45) Date of Patent: May 19, 2015

(54) METHOD AND DEVICE FOR DIFFUSE EXCITATION IN IMAGING

(75) Inventors: Laurent Guyon, Grenoble (FR); Jérôme Boutet, Claix (FR); Mathieu Debourdeau, St. Pierre d'Allevard (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 653 days.

(21) Appl. No.: 12/898,072

(22) Filed: Oct. 5, 2010

(65) Prior Publication Data

US 2011/0085721 A1 Apr. 14, 2011

(30) Foreign Application Priority Data

Oct. 8, 2009 (FR) ...................................... 09 57029

(51) Int. Cl.
*A61B 1/07* (2006.01)
*A61B 5/00* (2006.01)
*G01N 21/64* (2006.01)

(52) U.S. Cl.
CPC ................. *A61B 5/0073* (2013.01); *A61B 1/07* (2013.01); *A61B 5/6843* (2013.01); *G01N 21/645* (2013.01)

(58) Field of Classification Search
USPC ........................... 385/116–119; 600/476, 478
See application file for complete search history.

(56) References Cited

U.S. PATENT DOCUMENTS

| | | | |
|---|---|---|---|
| 5,824,023 A * | 10/1998 | Anderson | 607/88 |
| 6,058,324 A | 5/2000 | Chance | |
| 6,138,046 A * | 10/2000 | Dalton | 600/476 |
| 6,304,771 B1 | 10/2001 | Yodh et al. | |
| 6,825,930 B2 | 11/2004 | Cronin et al. | |
| 7,304,724 B2 * | 12/2007 | Durkin et al. | 356/73 |
| 7,321,791 B2 | 1/2008 | Levenson et al. | |
| 7,477,931 B2 | 1/2009 | Hoyt | |
| 7,675,044 B2 | 3/2010 | Laidevant et al. | |
| 8,116,845 B2 * | 2/2012 | Hashimshony et al. | 600/421 |
| 2002/0072677 A1 | 6/2002 | Sevick-Muraca et al. | |
| 2005/0065440 A1 | 3/2005 | Levenson | |
| 2005/0226548 A1 | 10/2005 | Durkin et al. | |
| 2005/0264805 A1 | 12/2005 | Cromwell et al. | |
| 2006/0149479 A1 | 7/2006 | Ma | |
| 2008/0051665 A1 | 2/2008 | Xu et al. | |
| 2008/0200780 A1 | 8/2008 | Schenkman et al. | |

(Continued)

FOREIGN PATENT DOCUMENTS

EP 1 884 765 A1 2/2008
EP 2 063 257 A2 5/2009

(Continued)

OTHER PUBLICATIONS

French Preliminary Search Report issued May 31, 2010, in Patent Application No. 0957029 (with Translation of Category of Cited Documents in the attached foreign language Search Report).

(Continued)

*Primary Examiner* — Michelle R Connelly
(74) *Attorney, Agent, or Firm* — Oblon, McClelland, Maier & Neustadt, L.L.P.

(57) ABSTRACT

A coupling device for an optical fiber used in optical tomography examination of a medium includes a mass of diffusing material for a wavelength guided by the optical fiber. This mass includes a bearing surface to be applied against the surface of the medium. At least one housing is provided in the mass to receive the end of the optical fiber.

19 Claims, 10 Drawing Sheets

(56) References Cited

U.S. PATENT DOCUMENTS

| | | | |
|---|---|---|---|
| 2009/0046291 A1* | 2/2009 | Van Der Mark et al. | 356/440 |
| 2009/0065710 A1 | 3/2009 | Hunziker et al. | |
| 2009/0131931 A1 | 5/2009 | Lee et al. | |
| 2009/0141959 A1 | 6/2009 | Can et al. | |
| 2009/0153850 A1 | 6/2009 | Nielsen et al. | |
| 2009/0245611 A1 | 10/2009 | Can et al. | |
| 2010/0155599 A1* | 6/2010 | Godavarty et al. | 250/334 |
| 2011/0013006 A1* | 1/2011 | Uzenbajakava et al. | 348/77 |
| 2011/0105865 A1* | 5/2011 | Yu et al. | 600/310 |

FOREIGN PATENT DOCUMENTS

| | | | |
|---|---|---|---|
| GB | 2 231 958 A | 11/1990 | |
| JP | 10-511875 | 11/1998 | |
| JP | 2009-148550 | 7/2009 | |
| WO | WO 96/20638 * | 7/1996 | A61B 5/00 |
| WO | WO 9620638 A1 * | 7/1996 | |
| WO | WO 96/26431 | 8/1996 | |
| WO | WO 01/09605 A1 | 2/2001 | |
| WO | WO 01/50955 A1 | 7/2001 | |
| WO | WO 2005/040769 A2 | 5/2005 | |
| WO | WO 2005/043138 A1 | 5/2005 | |
| WO | WO 2006/032151 A1 | 3/2006 | |
| WO | WO 2006/087437 A2 | 8/2006 | |
| WO | WO 2006/135769 A1 | 12/2006 | |
| WO | WO 2008/132522 A1 | 11/2008 | |

OTHER PUBLICATIONS

Huiyuan He, et al., "An analytic, reflection method for time-domain florescence diffuse optical tomography based on a generalized pulse spectrum technique", Proceedings of SPIE, vol. 6850, XP 002579460, 2008, pp. 1-8.

S. R. Arridge, "Optical tomography in medical imaging", Inverse Problems, vol. 15, No. 2, Apr. 1999, pp. R41-R93.

Qizhi Zhang, et al., "Three-dimensional diffuse optical tomography of simulated hand joints with a 64 × 64-channel photodiodes-based optical system", Journal of Optics A: Pure and Applied Optics, vol. 7, No. 5, 2005, pp. 224-231.

A. Cichocki, et al.,"Multlilayer nonnegative matrix factorisation", Electronics Letters, vol. 42, No. 16, XP 6027125, Aug. 3, 2006, pp. 1-2.

Laurent Guyon, et al., "Time-Resolved Fluorescence Tomography in Cancer Research: Backward Versus Toward Geometry", vol. 7174, XP 002579495, Feb. 12, 2009, pp.1-11.

Michael S. Patterson, et al., "Time resolved reflectance and transmittance for the non-invasive measurement of tissue optical properties", Applied Optics, vol. 28, No. 12, Jun. 15, 1989, pp. 2331-2336.

Jun Wu, et al., "Fluorescence tomographic imaging in turbid media using early-arriving photons and Laplace transforms", Proceedings of the National Academy of Sciences USA, vol. 94, Aug. 1997, pp. 8783-8788.

Aurélie Laidevant, et al., "Experimental study of time-resolved measurements on turbid media: determination of optical properties and fluorescent inclusions characterization", European Conferences on Biomedical Optics, vol. 5859, Jun. 12-16, 2005, pp. 1-9.

Jean-Marc Dinten, et al., "Performance of different reflectance and diffuse optical imaging tomographic approaches in fluorescence molecular imaging of small animals", Medical Imaging, Proceedings of SPIE, vol. 6142, 2006, pp. 1-10.

Anand T. N. Kumar, et al., "Fluorescence-lifetime-based tomography for turbid media", Optics Letters, vol. 30, No. 24, Dec. 15, 2005, pp. 3347-3349.

S. Lam, et al., "Time Domain Fluorescent Diffuse Optical Tomography: analytical expressions", Optics Express, vol. 13, No. 7, Apr. 4, 2005, pp. 2263-2275.

F. Gao, et al., "Time-Domain Fluorescence Molecular Tomography Based on Generalized Pulse Spectrum Technique", Proceedings Biomed., 2006, pp. 1-3.

Jeffrey C. Lagarias, et al., "Convergence Properties of the Nelder-Mead Simplex Method in Low Dimensions", Society for Industrial and Applied Mathematics, Journal on Optimization, vol. 9, No. 1, 1998, pp. 112-147.

S. R. Arridge, et al., "The theoretical basis for the determination of optical pathlengths in tissue: temporal and frequency analysis", Phys. Med. Biol., vol. 37, No. 7, 1992, pp. 1531-1560.

R. Cubeddu, et al., "Imaging of optical inhomogeneities in highly diffusive media: Discrimination between scattering and absorption contributions", Appl. Phys. Lett., vol. 69, No. 27, Dec. 30, 1996, pp. 4162-4164.

Christoph Bremer, et al., "Optical-based molecular imaging: contrast agents and potential medical applications", Eur. Radiol, vol. 13, 2003, pp. 231-243.

Anuradha Godavarty, et al., "Three-dimensional fluorescence lifetime tomography", Med. Phys., vol. 32, No. 4, Apr. 2005, pp. 992-1000.

Amir H. Gandjbakhche, et al., "Effects of multiple-passage probabilities on fluorescent signals from biological media", Applied Optics, vol. 36, No. 19, Jul. 1, 1997, pp. 4613-4619.

David Hall, et al., "Simple time-domain optical method for estimating the depth and concentration of a fluorescent inclusion in a turbid medium", Optics Letters, vol. 29, No. 19, Oct. 1, 2004, pp. 2258-2260.

Aurélie Laidevant, et al., "Effects of the surface boundary on the determination of the optical properties of a turbid medium with time-resolved reflectance", Applied Optics, vol. 45, No. 19, Jul. 1, 2006, pp. 4756-4764.

Aurélie Laidevant, et al., "Analytical method for localizing a fluorescent inclusion in a turbid medium", Applied Optics, vol. 46, No. 11, Apr. 10, 2007, pp. 2131-2137.

Adam Liebert, et al., "Evaluation of optical properties of highly scattering media by moments of distributions of times of flight of photons", Applied Optics, vol. 42, No. 28, Oct. 1, 2003, pp. 5785-5792.

Maureen A. O'Leary, "Imaging With Diffuse Photon Density Waves", Faculties of the University of Pennsylvania, 1996, pp. 1-192.

Vasilis Ntziachristos, et al., "Experimental three-dimensional fluorescence reconstruction of diffuse media by use of a normalized Born approximation", Optics Letters, vol. 26, No. 12, Jun. 15, 2001, pp. 893-895.

Eva M. Sevick-Muraca, et al., "Origin of phosphorescence signals reemitted from tissues", Optics Letters, vol. 19, No. 23, Dec. 1, 1994, pp. 1928-1930.

U.S. Appl. No. 14/123,352, filed Dec. 2, 2013, Boutet, et al.

Office Action mailed Sep. 1, 2014 in Japanese Patent Application No. 2010-227508 (with English-language Translation).

* cited by examiner

FIG.10B

METHOD AND DEVICE FOR DIFFUSE EXCITATION IN IMAGING

TECHNICAL FIELD AND PRIOR ART

The invention concerns the field of diffuse optical imaging applied to the medical sphere and notably in vivo and ex vivo fluorescence imaging.

These techniques can be used to implement non-invasive diagnosis systems through the use of non-ionizing radiation, which are easy to use and low cost.

One application of diffuse optical imaging is fluorescence imaging, in which a fluorescent marker or fluorophore (chemical substance of a molecule capable of emitting fluorescent light after excitation) is injected into a subject to be examined and fixes itself to certain specific molecules e.g. cancerous tumours. The region of interest is illuminated at the optimal excitation wavelength of the fluorophore. A fluorescence signal is then detected.

A diffuse optical imaging technique also exists without the injection of a fluorescent marker. In this case, it is sought to analyze a signal at the same wavelength as the excitation wavelength.

Figure 1:
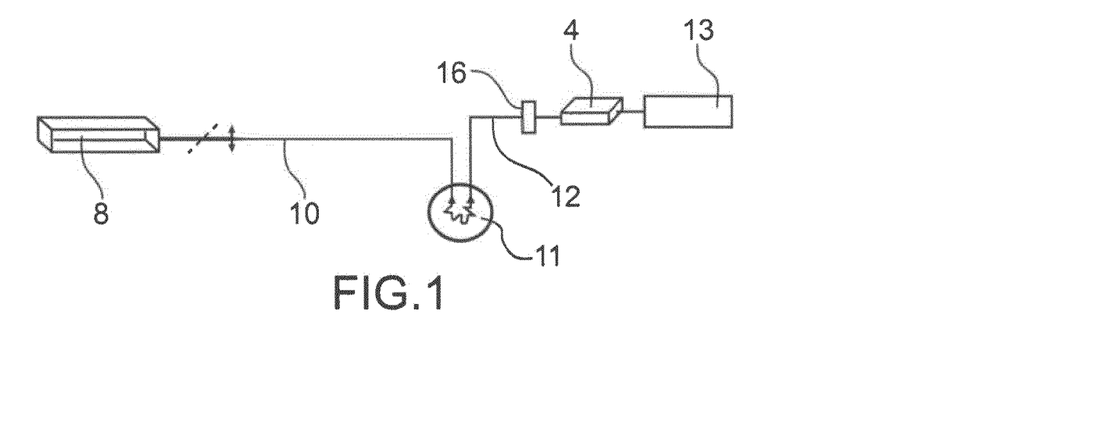
FIG. 1 illustrates a device to implement a method according to the prior art.

One example of a device for implementing one of these fluorescence tomography techniques is illustrated FIG. 1.

An excitation laser 8, e.g. in titanium sapphire, delivers a pulse train at a certain repeat rate, for example 80 Mhz, with a mean power of a few hundred milliwatts output from the excitation fibre 10. This laser can be wavelength tuned to excite different types of fluorophores. The laser, injected into the excitation optical fibre 10, allows probing of the sample 11, a diffusing medium in which a fluorescent marker is or is not included depending on the type of technique used.

If a fluorescent marker is present in the medium, the fluorescence it emits is collected by a second—detection—optical fibre 12 and the filtered fluorescence signal (reference 16 designates a filter) is measured using a detector e.g. a photomultiplier tube 4 connected to means 13 allowing the fluorescence signal to be measured.

If there is no fluorescent marker, then the examination is a diffuse optical examination, and it is the diffused signal which is collected by the second optical fibre 12, the filter 16 then being adapted to the excitation wavelength.

Whatever the technique used, to achieve better sensitivity there is a possible temptation to inject high laser energy into the examined medium. However a problem of damage to this medium arises above a certain energy density. This is notably the case when working on a tissue and notably on a living tissue e.g. a tissue of a human organ (breast, prostate, brain, testicles, arms, carotid, thyroid . . . )

It is possible to endeavour to widen the pulse geometrically. However, in addition to the fact that the tissues will evacuate heat less easily, the resolution of the image will be deteriorated on and after a fibre 10 diameter of the order of 1 mm.

Another problem is the problem of sensitivity: it is desired to achieve the best collection of the photons emanated by the examined medium 11. It is effectively sought to minimize losses, notably at the interfaces.

Another problem relates to edge effects which hamper reconstruction, these being difficult to model accurately. It is therefore ascertained that the boundaries of the medium are a source of error when reconstructing the properties of the medium.

DISCLOSURE OF THE INVENTION

The invention first concerns a coupling device to couple at least one optical fibre with a view to optical examination of a medium to be examined, the examination being of diffuse optical imaging type, comprising:
- a matrix or mass in diffusing material for a wavelength guided by the optical fibre, this mass comprising a bearing surface to be applied against the surface of the medium to be examined,
- at least one optical fibre of which one end is arranged permanently in the diffusing material and/or at least one housing provided in the mass and capable of receiving the end of an optical fibre.

In the remainder hereof, the expressions matrix or mass or diffusing matrix or diffusing mass are used indifferently.

When in use, the matrix is placed in contact with the sample or examined organ.

Said device may comprise:
- at least two housings, each housing being capable of receiving the end of an optical fibre,
- or at least one fibre of which one end is arranged permanently in the diffusing material, and at least one housing capable of receiving the end of an optical fibre,
- or at least two fibres, each having one end arranged permanently in the diffusing material.

More generally, any number of housings and/or fibre ends can be provided in the same matrix, the housing(s) being intended to receive one or more fibres (excitation and/or collection fibres).

In particular a signal collecting fibre, whether a fluorescence or diffusion signal, can be inserted permanently or in a housing inside the diffusing matter of the mass or matrix. In this case, improved efficacy of signal collection is ascertained compared with the case in which this fibre is located outside the coupling device of the invention.

The effect of using a matrix is to distance the boundary of the medium from the ends of the excitation fibre(s) and/or collection fibre(s), which limits the perturbation related to edge effects. With a thick matrix, whose thickness (along a direction substantially perpendicular to the bearing surface) exceeds a few cm, e.g. greater than 3 cm or 5 cm, the influence of the edges becomes negligible; the conditions are then close to those of an infinite medium which subsequently facilitates and improves the reconstruction of the optical properties of the medium.

Preferably:
- one of the housings has a bottom located at a distance (h) from the bearing surface that is shorter than the distance (H) at which the bottom of at least one other housing and/or the end of a fibre is located,
- and/or one of the fibres has one end arranged permanently in the diffusing mass, at a distance (h) from the bearing surface that is shorter than the distance (H) at which the bottom of at least one other housing is located and/or the end of another fibre is located.

Therefore, it is possible to position the end of one or more excitation fibres further from the interface with the examined medium than the end of one or more collection fibres, to maximize the collected energy. According to one preferred embodiment, the height h is chosen to be zero for at least one collection fibre, so that at least one collection fibre is in contact with the medium, or as close as possible thereto, to maximize the collected energy.

If a fibre, which transmits an excitation or incident signal, is inserted in a housing of the matrix or the mass in diffusing material, or if its end is contained permanently in this mass, said mass diffuses the excitation radiation. This diffusion is similar to that of the examined medium, if the diffusing medium has optical properties close to those of the examined medium. By close is meant a relative deviation of less 30%, preferably 20%, for at least one of the parameters under consideration: absorption coefficient or reduced diffusion coefficient.

In this case, the interface and the medium examined can be considered as a single diffusing medium. Additionally, this simplifies calculations during the reconstruction step.

Preferably, the diffusing medium therefore has absorption and reduced diffusion coefficients $\mu_a$ and $\mu_{s'}$ close to those of the tissues of the examined medium.

The diffusing material, for example, therefore has a reduced diffusion coefficient $\mu_{s'}$ greater than 0.1 cm$^{-1}$ and less than 700 cm$^{-1}$, and preferably between 1 and 50 cm$^{-1}$, and further preferably between 5 and 20 cm$^{-1}$ It may have an absorption coefficient $\mu_a$ greater than 0.01 cm$^{-1}$ and less than 10 cm$^{-1}$. Preferably, this coefficient is lower than the reduced diffusion coefficient $\mu_s'$. Preference is given to values of between 0.01 cm$^{-1}$ and 1 cm$^{-1}$.

An absorbent layer may cover the mass in diffusing material, in part or at least in part. This may be a layer of black paint or of anodized metal partly covering or at least partly covering the matrix. Preferably, the contact surface with the medium is free of this layer.

The spot of the excitation beam, on the bearing surface intended to be in contact with the object to be examined, preferably has a surface area $S_t$ of between 1 mm$^2$ and 1 cm$^2$ or a few cm$^2$, for example 5 cm$^2$, or of the order of about ten cm$^2$ or a few tens of cm$^2$, for example lying between 10 cm$^2$ and 20 cm$^2$ or 50 cm$^2$.

According to another particular embodiment of the invention, the bearing surface further comprises one or more protuberances of substantially rounded shape with no sharp edges, extending the bearing surface that is to be applied against the object to be examined.

Said device may advantageously comprise at least one housing, or the end of at least one fibre, whose bottom is located substantially in or at said protuberance.

According to the invention, the excitation or incident beam is brought from a source, generally a point source located outside or inside the diffusing mass, but the tissue is broadly illuminated due to the diffusion of the excitation signal in the diffusing mass.

The source or the source point may have a diameter of less than 3 mm, preferably less than 500 μm, whilst the tissue is illuminated by a spot with a diameter of at least 1 mm or 5 mm or 10 mm, preferably less than 20 mm or than 5 cm. This point source may be located in the matrix, this case notably corresponding to an optical fibre of which one end is included in the diffusing mass, this end then possibly being likened to the point source. This is particularly the case when the excitation fibre has its end inserted in an opening provided in the diffusing mass, or the case in which the excitation fibre has its end fixed permanently in the diffusing mass e.g. by moulding. However, the light source in some cases may be located at a distance away from the diffusing mass.

An end portion of one of the fibres may only comprise a core if the matrix acts as cladding.

A further subject of the invention is a diffuse optical imaging device, notably for fluorescence imaging of a medium, comprising:

a) means e.g. a laser forming a radiation source to form incident radiation on the medium, at least at a first wavelength, b) a coupling device according to the invention, comprising an optical fibre of which one end is arranged permanently in the diffusing mass, or comprising an optical fibre arranged in the housing provided in the mass of diffusing material, c) detection means to detect a diffused or fluorescence signal, derived from the medium being examined.

This optical fibre of the coupling device may be a collection optical fibre to collect a signal emanated by a medium, and to convey it towards the detection means.

Said device may further comprise an excitation optical fibre to bring the incident radiation onto to the medium to be examined.

The optical fibre, or an optical fibre, of the coupling device may be an excitation optical fibre to bring the incident radiation onto the medium to be examined.

One particular embodiment is also a case in which an excitation light source, such as a laser or optical fibre, is positioned at a distance from the diffusing matrix and the corresponding radiation is sent towards the medium to be examined by passing through the matrix, one or more collection fibres being positioned in a matrix according to the invention, either permanently or temporarily.

One particular embodiment is also the case in which an excitation light source, such as a laser or optical fibre, is located at a distance from the diffusing matrix and the corresponding light radiation is sent towards the medium to be examined without passing through the matrix, one or more collection fibres being positioned in a matrix according to the invention, permanently or temporarily.

The radiation source may be a pulsed, continuous-time or amplitude-modulated source. The diffuse optical imaging technique applied may be of time-resolved type, or any other type. This technique can be applied to fluorescence diffuse optical imaging e.g. fluorescence tomography, or to the determination of the optical properties of diffusing media.

A further subject of the invention is an examination method of diffuse optical imaging type, to examine part of a medium, in which at least one coupling device of the invention is used and wherein:

the coupling device is applied against this medium,
the medium is illuminated or optically excited by the means forming a radiation source, to form incident radiation on the medium and then to cause this incident radiation to enter the medium,
an optical signal emanated by the medium is collected by means of at least one collection optical fibre.

Preferably, a fluid is applied between the bearing surface of the diffusing medium of the coupling device and the surface of the medium to be examined.

With or without coupling fluid it was able to be ascertained, unexpectedly, that if the medium to be examined has certain flexibility, for example as with living tissues, the exertion of a pressure on the coupling device positioned against the medium to be examined makes it is possible to increase the reception signal. When implementing a device according to invention, comprising at least one excitation fibre and/or at least one collection fibre, pressure may then advantageously be applied to place the coupling device against the examined medium, so as to cause a fluid contained in this medium to flow outside part of this medium towards a region located on the periphery of the coupling device.

DETAILED DESCRIPTION OF PARTICULAR EMBODIMENTS

Figure 2:
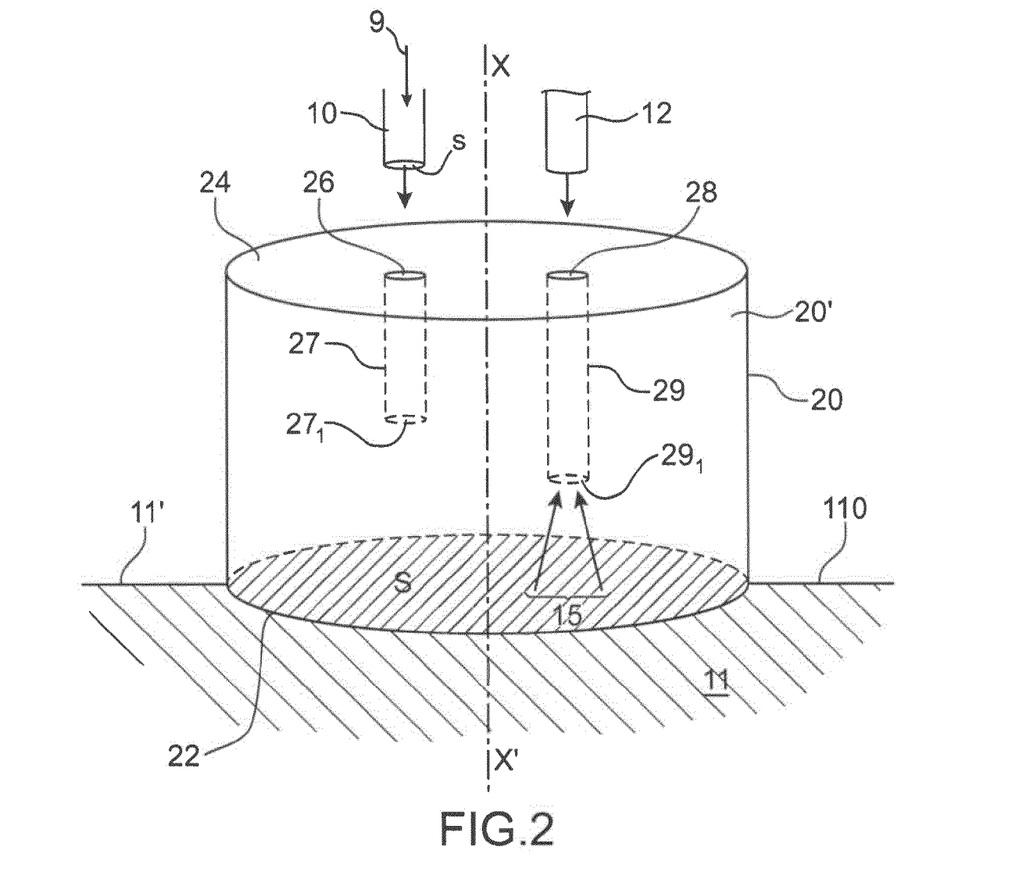
FIG. 2 is an example of an embodiment of the invention, with a cylindrical diffusion matrix, FIG. 3 gives an example of another embodiment of the invention, with a substantially hemispherical diffusion matrix.

A first example of an embodiment of the invention is given FIG. 2.

This figure illustrates the fibres 10, 12 which respectively bring an excitation beam 9 (or more generally an incident beam) into a diffusing medium to be examined 11, and collect a fluorescent or diffusion signal emanated by this same medium.

In this example, the ends of the two fibres 10, 12 are inserted in an interface element 20 in diffusing material. In the remainder hereof the expression <<matrix>> will be used, but either of the terms <<interface>> or <<mass>> may be used indifferently in its stead. This matrix may be in a solid material, but it can also be in a soft, viscous or liquid material, in which case it is intralipid for example.

The matrix here is of substantially cylindrical shape, having two faces 22, 24 perpendicular to the axis XX' of revolution of the cylinder. One of these faces (face 24 in FIG. 2) comprises two openings 26, 28 for two cavities or housings 27, 29. These housings are intended to receive the ends of the two excitation 10 and collection 12 fibres when they are inserted via the openings 26, 28. In other words, each of the openings 26, 28, which are preferably substantially circular, is extended in the mass of diffusing material of the matrix 20 by a wall defining a cavity 27, 29 which is preferably substantially cylindrical adapted to the fibre. Each cavity has one closed end $27_1$, $29_1$ facing the surface 22 intended to be in contact with the medium 11 to be examined.

Each closed end $27_1$, $29_1$ is also the part of the housing 27, 29 closest to this surface 22. Via the end $27_1$, the excitation beam 9 leaves the excitation fibre 10 and enters the matrix; via the end $29_1$ the diffusion beam 9 leaves the matrix and is collected by the collection fibre 12. Each cavity thus defined in the matrix is adapted to receive at least one fibre. The diameter of each opening 26, 28 is therefore substantially the diameter of the fibre or fibres it is intended to receive. A coupling liquid can be placed at the bottom of either one and/or both of the cavities; the refractive index of this liquid is preferably close to that of the matrix material.

Advantageously, to improve the optical coupling between the matrix and the medium 11 being examined, and hence to facilitate modelling of the propagation of light rays in the diffusing system consisting of the matrix and medium 11, the optical properties of diffusion and optionally of absorption of the matrix material can be chosen to be close to those of the medium to be examined.

Therefore the reduced diffusion coefficient µ's of the constituent material of the matrix may be greater than 0.1 cm$^{-1}$ and is preferably between 1 cm$^{-1}$ and 700 cm$^{-1}$, more preferably between 1 and 50 cm$^{-1}$, and further preferably between 5 and 20 cm$^{-1}$, these values being well adapted to excitation or fluorescence wavelengths in the red or infrared.

The absorption coefficient $\mu_a$ of the matrix constituent material may vary between 0 cm$^{-1}$ and 10 cm$^{-1}$ and preferably between 0.01 cm$^{-1}$ and 1 cm$^{-1}$ which, again, are well adapted to excitation or fluorescence wavelengths in the red or infrared.

With a low absorption coefficient $\mu_a$ it is possible to prevent too much signal loss and excessive heating of the matrix (any absorption leads to a rise in temperature). Preferably a matrix 20 is formed having the same absorption coefficient $\mu_a$ as the examined matter 11 in order to form the most homogeneous medium possible, with a view to reducing the influence of the interface and facilitating reconstruction. Therefore, in some cases, a low absorption coefficient will be chosen, whilst in other applications an absorption coefficient will be preferred that is close to that of the medium under consideration.

A composition of titanium dioxide ink resin type is a suitable material. It is also possible to use a diffusing polymer or a transparent polymer to which diffusing particles are added, or cryogel. Cryogel is a polyvinyl alcohol compound often abbreviated to PVA whose consistency can be more made more or less viscous and even solid, by subjecting it to freeze-defreeze cycles. As a variant, it is also possible to use viscous or solid materials containing agarose gel or animal gelatine. Preferably the refractive index of the material is chosen to be close to that of the medium examined.

The excitation radiation 9 used may notably be in the infrared, for example having a wavelength or wavelengths of between 400 nm and 1300 nm, preferably between 600 nm and 950 nm. The collected signal 15 either has a wavelength that is greater than the wavelength or wavelengths of the excitation beam (for a fluorescence signal derived from an exogenous marker) or a wavelength substantially identical or close to the wavelength(s) of the excitation beam (as with a diffusion signal).

The surface 22, or a bearing face, allows the device to be applied against the surface 11' of the medium 11 to be examined. In general, this surface 22 is planar, enabling it to be applied against a surface which itself is at least partly planar.

However, it may also be curved or contain a curve; it will be seen below that other surfaces are suitable, in particular for the examination of soft or flexible tissues, with protuberances having rounded shapes or with at least one non-zero radius of curvature in a plane perpendicular to the surface of the medium to be examined.

The matrix 20 may be of cylindrical shape as in FIG. 2: it then has an outer surface 20' with symmetry of revolution about an axis XX', substantially perpendicular to the surface 22, but this is only an example and said symmetry is not necessarily present. The shape of the matrix is not limited to this example, and its surface that is not intended to be in contact with the medium or tissue to be examined may be of cubic shape, or parallelepiped, or a semi-sphere, such as the surface 30' of the matrix 30 in FIG. 3, or according to another example it may have a curved surface 30', 40', 50' (see FIGS.

4-8D) and a planar surface 22, for example of semi-ellipsoid shape. In all cases, it may have at least one or at least two openings 26, 28, each extended by a cavity 27, 29 of substantially cylindrical shape adapted to receive one of the fibres.

Irrespective of the envisaged embodiment, the solid matrix has an outer surface 20', 30', 40', 50' which, during use, is intended not to be in contact with the surface of the examined medium. This surface can be partly coated with an absorbent layer 31, 41, 51 formed for example of a layer of dark paint, or a layer in anodized metal, but not in the opening regions 26, 28 which allow the fibre or fibres 10, 12 to be positioned in the matrix, and not on the surface 22 to be placed in contact with the medium to be analyzed.

Figure 3:
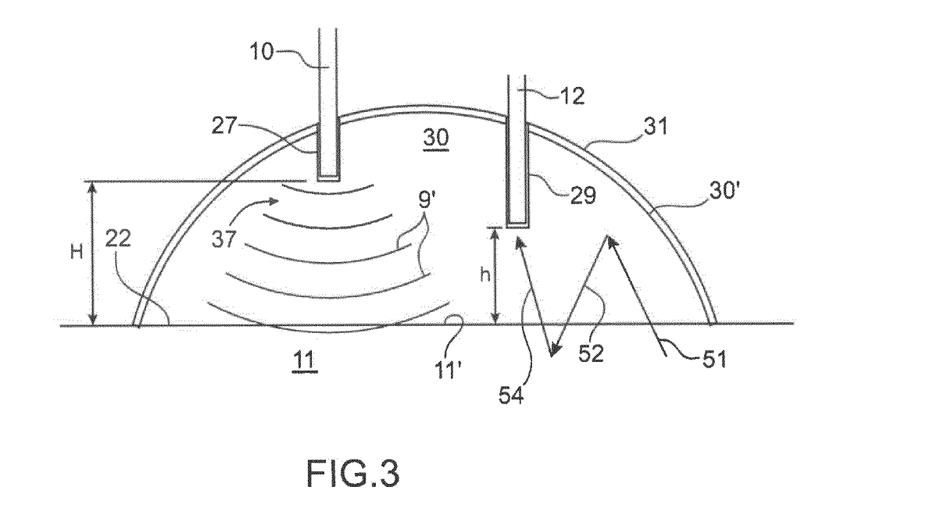
Figure 9A:
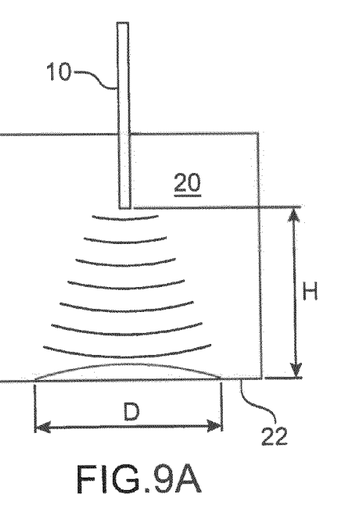
FIGS. 9A-9C show a matrix of a device according to the invention, a spot produced by illumination on the bearing surface of this matrix and an intensity profile along a section of this spot.
Figure 9B:
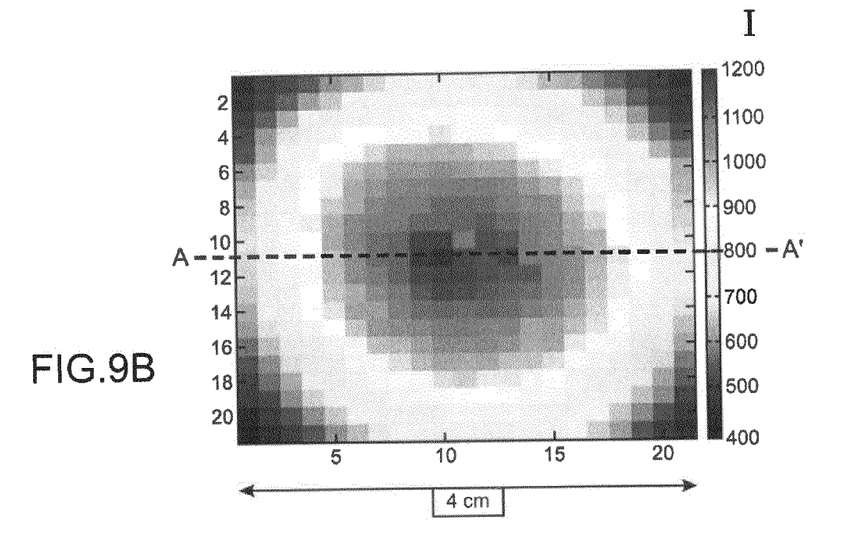
Figure 9C:
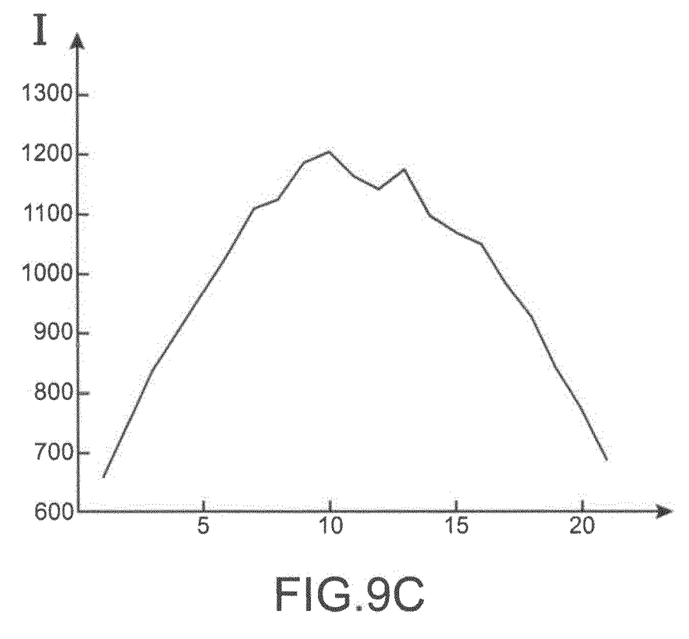

In general, if an excitation fibre 10 is inserted in a coupling device according to the invention, the source appears as a point in the diffusing medium of the matrix. However, there is a diffusion effect of the excitation radiation in this matrix, before it reaches the surface 11' of the examined medium 11. For example, FIG. 3 shows the diffusion of the excitation beam derived from the fibre 10, in the form of a wave 9' which diffuses from the end of this optical fibre before reaching the surface 11'. FIGS. 9A-9C, which are described below in more detail, give an example of the widening effect which can be obtained with a device according to the invention.

The impact of the incident beam on this medium is therefore not a point impact but distributed over a wider surface than if the fibre were used alone without the coupling device of the invention. The surface density of a signal is therefore lower than when excitation is directed with the same excitation signal intensity towards the medium to be examined without the device according to the invention.

Damage to the medium to be examined is therefore minimized and even avoided. However, the source is considered as remaining a point source and the laser beam or optical fibre can be modelled as being point sources. The diffusing matrix may also be taken into account in the model used for reconstruction, the diffusing medium incorporating the diffusing matrix.

Preferably, the depth of each housing 27, 29 is adapted to the function of the fibre it is to receive.

In particular, it is effectively preferable that the distance between the end of the excitation fibre 10 and the surface 11' of the matter to be analyzed should be longer than the mean free pathway of isotropic diffusion, the latter being the inverse of the coefficient of reduced diffusion ($=1/\mu_s'$) of the excitation photons in the diffusing medium.

Also, it was ascertained that it is preferable that the collection fibre should lie further ahead in the matrix than the excitation fibre, and therefore its end should lie fairly close to and preferably in contact with the surface 22

In general, irrespective of the embodiment, the surface 22 intended to be contact with the region which delimits the diffusing medium is preferably nearer the closed end $29_1$ of the cavity 29 intended to receive the signal collection fibre 12, than the closed end $27_1$ of the cavity 27 intended to receive the excitation fibre 10. In other words, the height H which separates the surface 22 from the end $27_1$ of the cavity 27, which end is the closest to this same surface, is greater than the height h which separates this surface 22 from the end $29_1$ of the cavity 29 the closest to the surface 22. For example, H lies between 0 and 5 cm, preferably between 1 mm and 10 mm, whilst h lies between 0 and 5 cm, preferably between 0 and 5 mm, and is more preferably close to 0.

The efficacy of signal collection is increased when the end of the collection fibre 12 is close to the interface 22. Some photons derived from the examined medium and effectively following the pathway referenced 51, 52, 54 (shown FIG. 3) and which are not directly directed towards the end of the fibre 12, will therefore be diffused in the mass of the matrix 20 and/or of the examined medium 11, and will therefore be brought back towards the end of fibre 12; they will undergo reflections or will be diffused in this mass of the matrix 20 or of the medium 11 (see the pathway 51-52-54 in FIG. 3) and part thereof will be captured by the fibre 12; these photons 51 would be lost for the signal if there were no diffusing material arranged between the medium 11 and the end $29_1$ of the collecting fibre.

Again preferably, the spot 37 of the excitation beam, such as illustrated FIG. 3, on the bearing face 22 intended to be contact with the object to be examined, has a surface area $S_t$ of the order of a few mm² to a few cm², even a few tens of cm², for example of between 10 mm² and 10 cm². It can be considered that the diameter of this spot of the excitation beam on the bearing face 22 is the width at mid-height of the maximum intensity of the diffusion spot. If this spot 27 is substantially circular its diameter, at the bearing face 22, is between 500 µm and 1 cm or a few cm, for example. At the output from the fibre 10, the diameter s of the light spot is a few hundred µm, for example between a few µm and a few hundred µm, even 1 mm. This is also valid for the other embodiments of the invention, provided an excitation fibre is inserted in the coupling device according to the invention.

By denoting s the surface of the end of the fibre and S the surface 22 of the diffusing matrix 20, the maximum authorized energy to be taken into account will be lower the greater the value of S, and the spatial resolution of reconstruction will notably depend on s. FIGS. 9A-9C provide an explanation for the widening of a beam entering into the examined medium 11 when using a device according to the invention (FIG. 9A), of the type described above in connection with FIG. 2, but in which only a single fibre namely the excitation fibre or incident beam 10 is inserted. The radiation which is sent into this fibre, on the output surface 22 intended to be in contact with the examined medium, forms a spot of diameter substantially equal to D. In this device, the fibre has a diameter of approximately 60 µm, and its end lies away from the surface 22 by a distance equal to about 6 cm. The $\mu_a$ and $p'_s$ coefficients of the matrix material are 0.03 cm⁻¹ and 9 cm⁻¹ respectively.

FIG. 9B shows an image of this spot in the plane of the surface 22, the intensity being displayed on the scale on the right side, at between 400 and 1200 in arbitrary units. FIG. 9C shows the intensity profile along an axis AA' which passes through the plane of this spot, substantially through the region of maximum intensity. It can be seen that, by means of this curve, it is possible to define a width at mid-height which here is about 4 cm. The diameter of the incident beam can be defined, at the surface 22, by this mid-height width. In this example, it can also be understood that the device according to the invention effectively allows the illumination surface of the incident beam to be increased considerably since, in this example, it increases from a diameter of 60 µm (on leaving the fibre 10) to a diameter of several centimeters. Evidently, the same widening effect of the excitation beam would be observed if the source were a fibre or a laser source located outside the matrix, but producing a beam e.g. a point beam passing through the matrix 30 before reaching the diffusing medium 11. In this case, one of the advantages of this diffusing matrix would again be found i.e. the widening of the incident beam, allowing a light source of high intensity to be used without causing any damage however to the examined medium. This technical effect derives from attenuation of the surface density of the signal resulting from widening of the excitation signal, this widening occurring under the effect of the diffusion of this excitation signal in the matrix 30, before reaching the medium 11.

In the above examples, the matrix comprises two openings and two housings, one for each of the fibres 10, 12.

Figure 4:
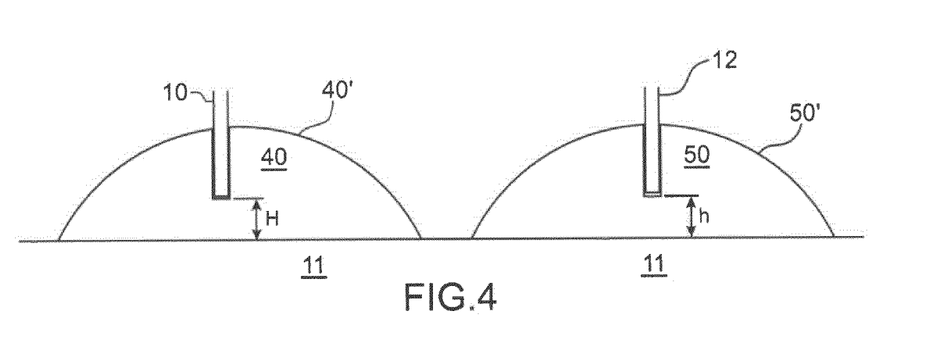
FIG. 4 is another example of another embodiment of the invention, with a diffusion matrix for each fibre, FIGS. 5A and 5B give an example of another embodiment of the invention, with two excitation fibres and one signal collection fibre, or two signal collection fibres and one excitation fibre.

As a variant, it is also possible to use a matrix for each fibre, as in FIG. 4: for an excitation fibre 10 and a collection fibre 12, two matrixes 40, 50 according to the invention are then used, positioned as desired on the surface of the object to be examined. Depending on the type of fibre (excitation or collection) inserted in each matrix, the fibre can enter to a greater or lesser depth into this matrix: the excitation fibre 10 may enter less deeply into a matrix 40 (depth H in FIG. 4), than the collection fibre 12 into matrix 50 (depth h<H in FIG. 4) to benefit from the above-described effects, notably to capture the radiation emanating from the examined medium. If several fibres are used, each bringing an excitation beam, several matrixes can be laid side by side, one for each beam, and one or more matrixes for signal collection.

Figure 5A:
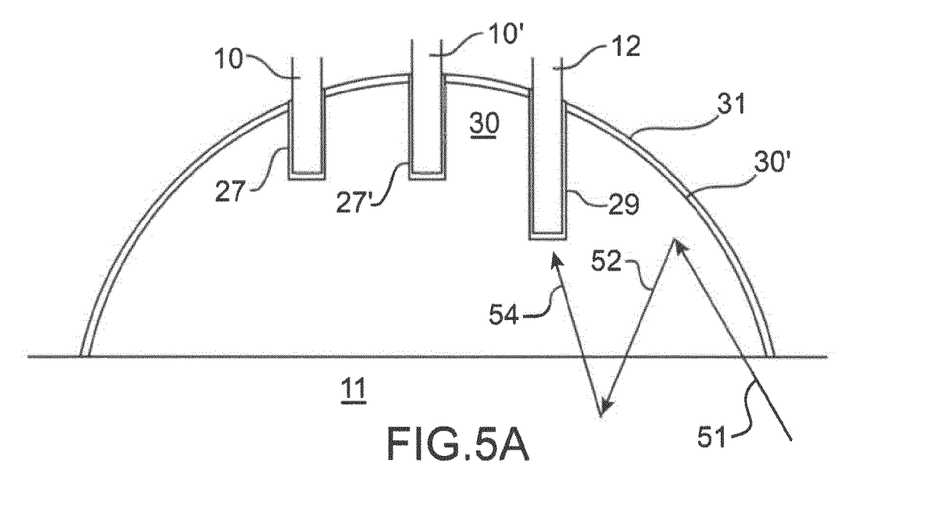

As a further variant, it is also possible to use one matrix for several fibres, as in FIG. 5A: for example several excitation fibres 10, 10' and one collection fibre 12 are positioned in the same matrix 30. However, it is also possible to have a single excitation fibre 10 and a plurality of collection fibres 12, 12' (FIG. 5B), but preferably a plurality of excitation fibres 10, 10', for example 1 to 100 excitation fibres and a plurality of collection fibres, for example 1 to 100 collection fibres.

Figure 5B:
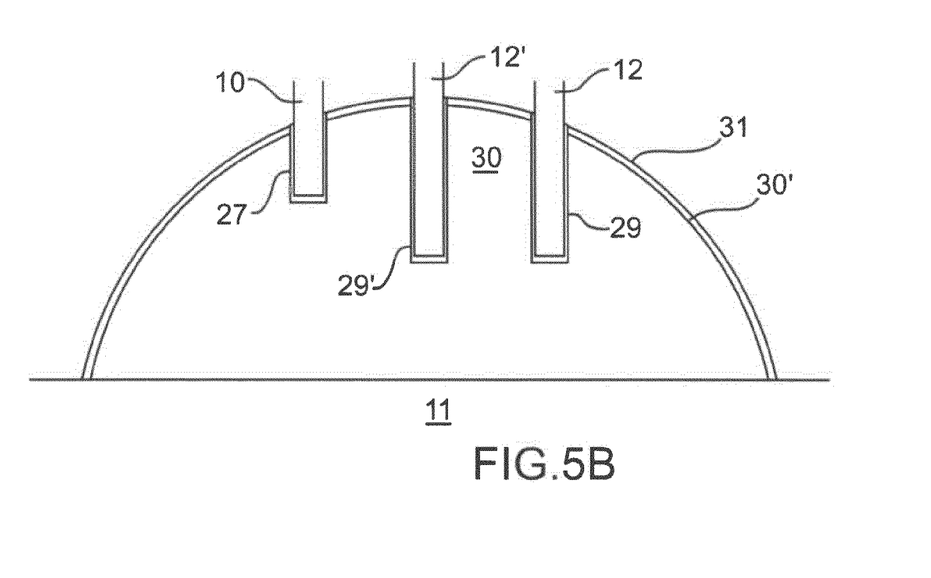

Here again, the depth of each housing is preferably adapted to the type of fibre to be received.

It is also possible (FIG. 6A) to have a matrix 40 comprising a single cavity 27, for example for an excitation fibre 10. The collection fibre 12 is then positioned outside the matrix, so that it can capture a fluorescence signal 15 or diffusion signal emanating from the medium 11. As a variant, a matrix 50 (FIG. 6B) comprises a single cavity 29 for a signal collection fibre 12. The excitation fibre 12 is then positioned outside the matrix, to convey an excitation signal 9, or there is no excitation fibre and the incident light radiation is brought directly from the source located at a distance from the matrix 50. It is preferably possible to make provision so that all or part of the light radiation produced by the source passes through part of the matrix 50, making it possible to maintain the technical effect of diffusion of the incident light signal in the matrix 50 before reaching the medium 11 to be examined. In other words, the light source can be a laser source or an optical fibre delivering a light beam directed towards the medium 11 and incident to the outer surface 50' of the matrix 50. With this embodiment, it is possible to draw benefit from the diffusion of the excitation signal in the matrix 50, as seen in the foregoing.

Figure 6A:
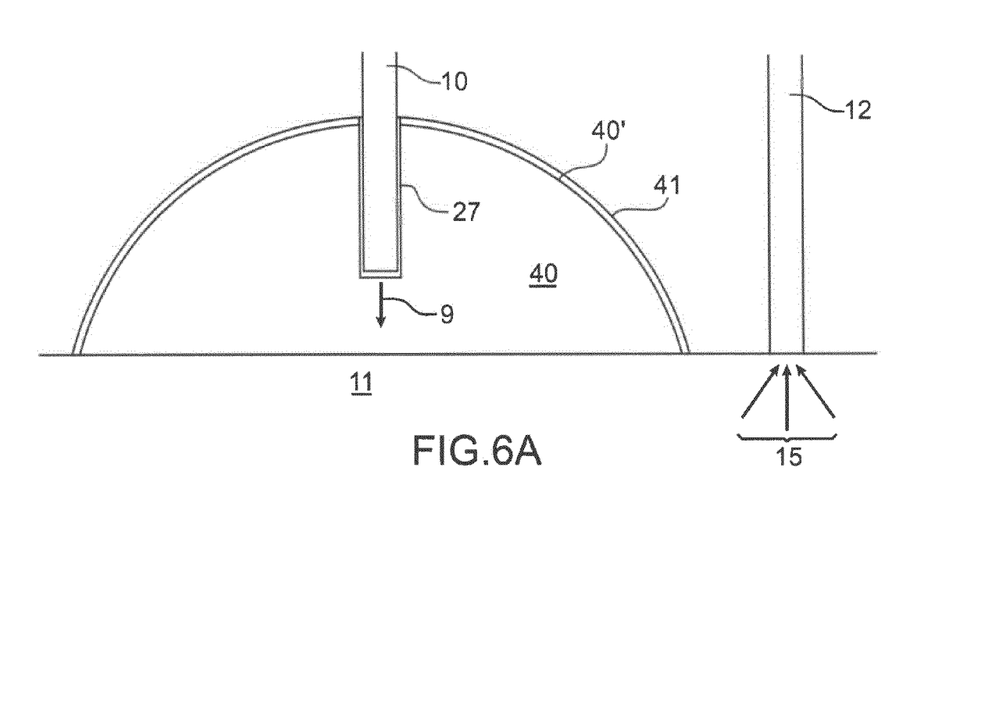
FIGS. 6A-6D are various examples of another embodiment of the invention, with one or more housings capable of receiving one or more excitation fibres (FIGS. 6A and 6C) or collection fibres collecting the fluorescence signal (FIGS. 6B and 6D)
Figure 6B:
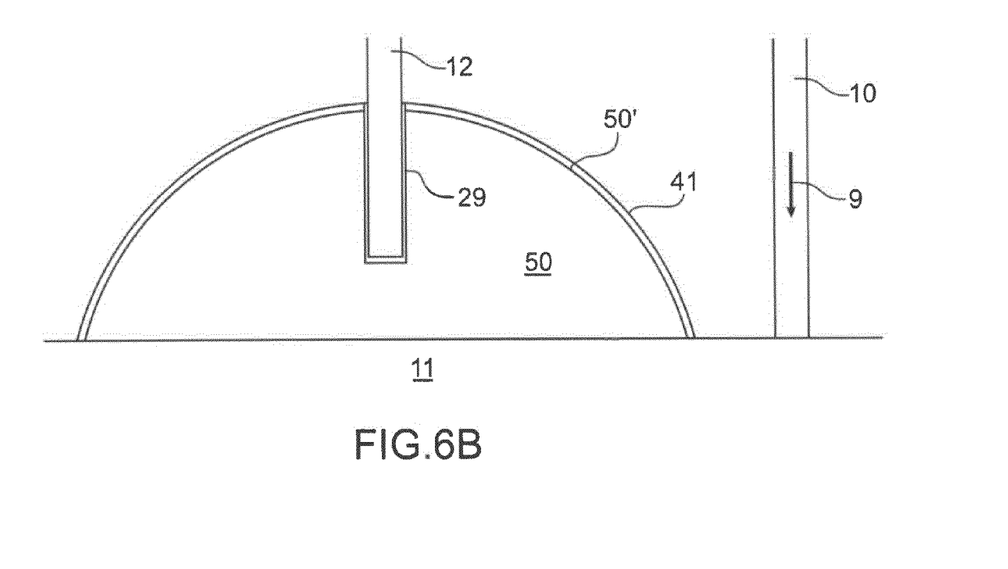
Figure 6C:
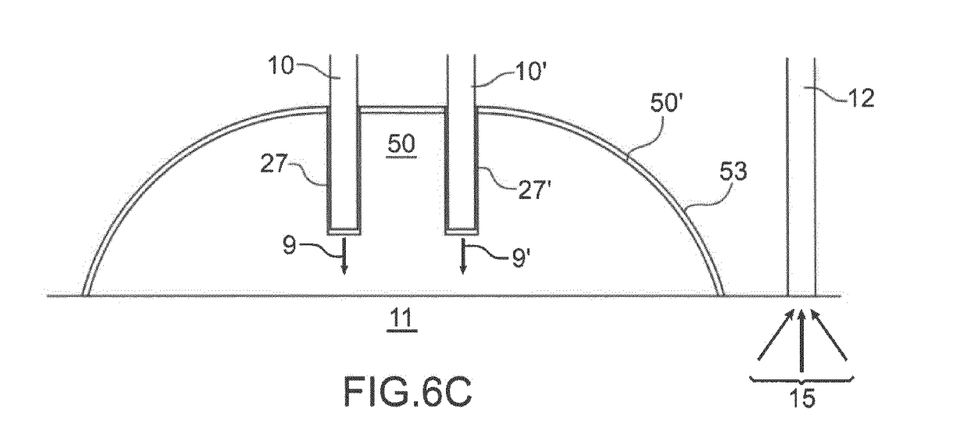
Figure 6D:
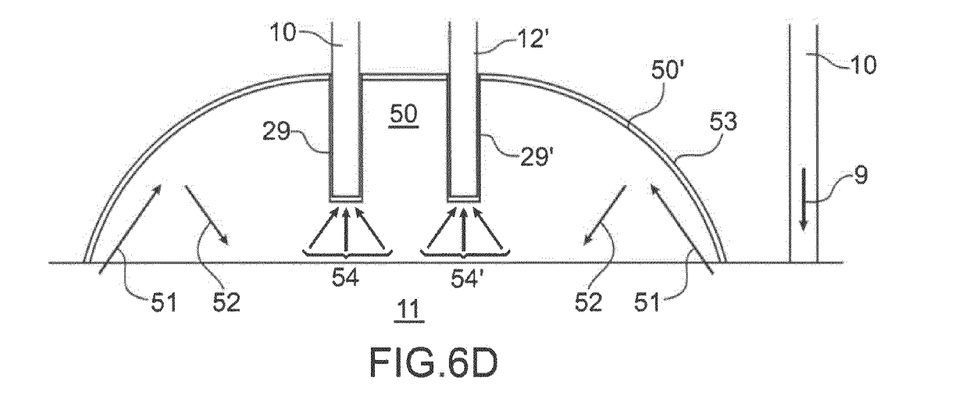

However, the excitation signal can also be directed towards the medium 11 without seeking diffusion in the matrix 40.

The depth of each cavity 27, 29 is preferably adapted to the type of fibre it receives, in relation to the above-mentioned considerations. A matrix 50 with two (or even more than two) excitation fibres 10, 10' is also feasible (FIG. 6C), whilst here too a collection fibre 12 is positioned outside the matrix. In this case, the collection fibre can be replaced by a detector, distant from the surface of the medium 11, but optically coupled with this surface so as to collect part of the light signal emerging from this surface. Similarly, a matrix 50 with two (or even more than two) collection fibres 12, 12' is feasible (FIG. 6D), whilst one or more excitation fibres 10 are positioned outside the matrix.

When the above-described device is in use, the surface 22 of the matrix or matrixes is applied against the sample to be analyzed. The fibre or fibres are inserted in the corresponding matrixes, for example before these are positioned against the sample.

Figure 10A:
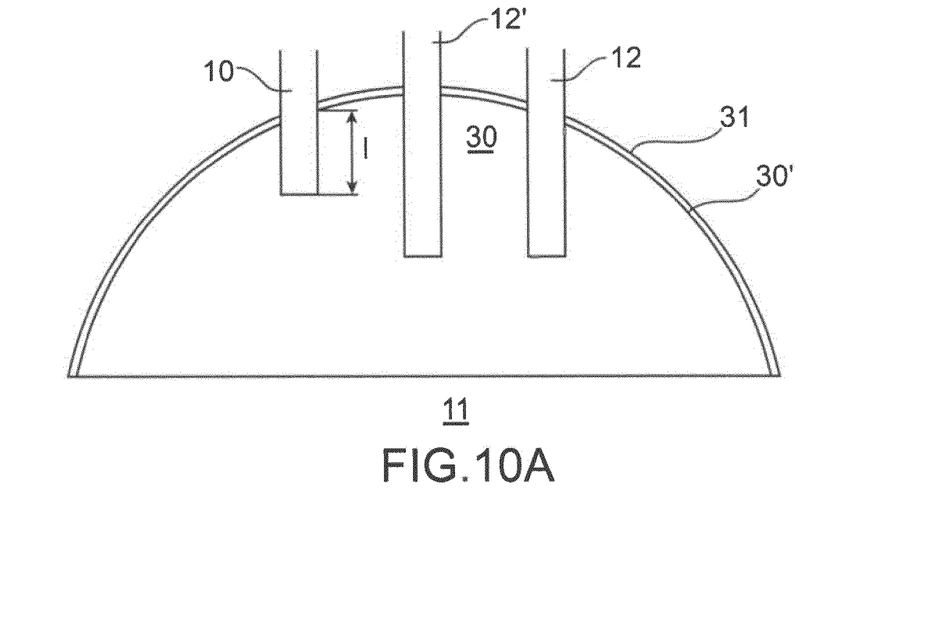
FIGS. 10A and 10B are examples of yet another embodiment of the invention, with fibres whose ends are arranged permanently in the material of the matrix.

According to another embodiment of the invention, of which an example is shown FIG. 10A, the fibre or fibres are integrated in the matrix at the time of its manufacture, for example by moulding. This allows better optical coupling between the end of each fibre and the matrix material. Consequently in this embodiment, when manufacturing the matrix, one or more housings are not prepared such as the housings 27, 29 in FIG. 2: the end of at least one optical fibre is permanently placed in the matrix material, for example over a length 1 (distance between the surface 30' of the diffusing mass, not intended to be applied against the examined medium 11, and the end of optical fibre arranged in this mass) of a few millimeters to a few centimeters, for example between 1 mm, or 5 mm, or 10 mm, and 1 cm, or 5 cm, or 10 cm. To obtain said device, it is possible to mould the material of the matrix around one or more optical fibres. Similarly, it is possible to integrate one or more fibres in a matrix which has the shape of any of those described above in connection with FIGS. 2-6D.

In this embodiment, the ends of the fibres are also placed, but permanently, at distances H and h which may have the characteristics and/or values explained above. The advantages, in optical terms, are the same as those described above for matrixes having housings in which the fibres are inserted. In particular, the widening effect of the incident beam is the same. Additionally, there is the same advantageous effect with a collection fibre 12 placed permanently in a matrix such as matrix 30, as the advantage described above in connection with FIG. 3, with the example of beams 51, 52, 54. The shape and/or the characteristics of the matrix material, and notably its type and/or its reduced diffusion coefficient and/or its absorption coefficient are preferably chosen from those already indicated above. The same applies to the incident radiation used and the preferred wavelength range in which it can be chosen, notably the infrared or near infrared. A device according to this embodiment is therefore <<ready-for-use>> i.e. when the matrix is positioned against the examined medium 11, it is not necessary also to perform an operation to insert the fibres into the housing(s) provided for this purpose in the matrix.

Figure 10B:
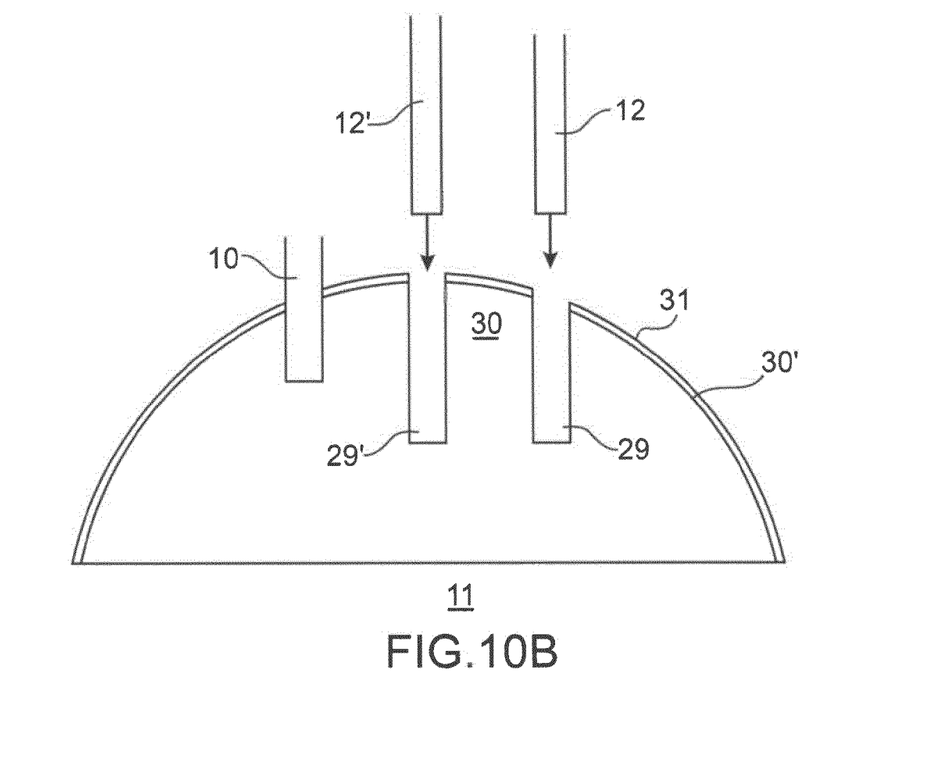

According to one variant of this other embodiment, a device according to the invention comprises a diffusing mass which permanently surrounds the end of one or more optical fibres, and also comprises a housing for the insertion of one or more other optical fibres. FIG. 10B for example illustrates an embodiment in which a fibre 10 is placed permanently in the mass 30 of diffusing material, whilst two collection fibres 12, 12' are to be inserted in corresponding housings 29, 29'. In the remainder hereof, the explanations given in connection with one of the embodiments, in which one or more fibres are inserted in one or more housings of a matrix, also apply to the other embodiment in which one or more fibres are incorporated or integrated in the matrix during the manufacture thereof, unless otherwise specified.

In one preferred embodiment of the invention, implemented for optical analysis, the incident light energy is brought towards the examined medium 11 via a fibre 10 for example. After propagation of the radiation to be analyzed in this medium, the energy is collected by measuring means 4, 13 that are provided e.g. a photomultiplier or camera such as a CCD camera, or CMOS, or CCD array, or one or more avalanche photodiodes, this energy being brought to the detector via a fibre for example or the detector lying distant from the surface 22 but optically coupled with this surface.

The assembly used may be the assembly shown FIG. 1, which can be used in combination with the coupling device of the present invention, but the invention also applies to cases in which the radiation source 8 is replaced by a continuous-time or amplitude-modulated source. In all cases, the laser can be wavelength tuned, for example from 400 nm to 1300 nm, preferably 600 to 950 nm to excite different types of fluorophores.

The system may further comprise digital processing means to process measured data e.g. a computer programmed for this purpose. An example of a method for time-resolved analysis of fluorescence imaging signals is given in document EP-1884765. This method can be used to reconstruct an image from a said device.

Figure 7:
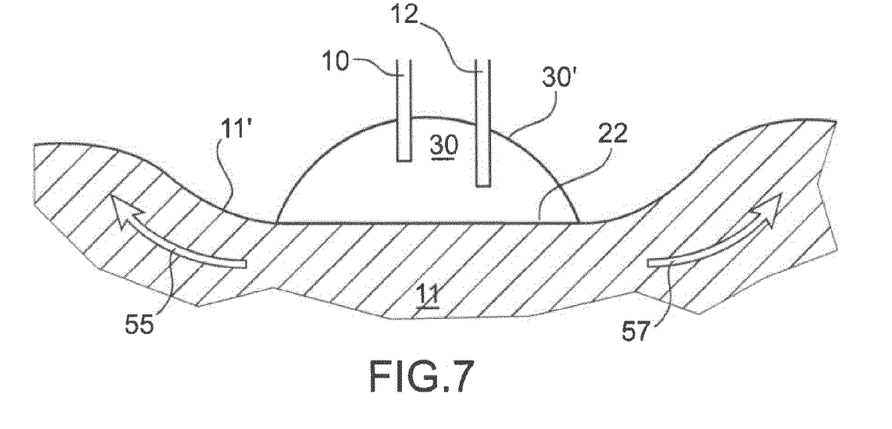
FIG. 7 illustrates one use of a device according to the invention, in which pressure is applied onto this device when it is in contact with the surface of a medium to be analyzed.

According to another aspect of the invention, for a medium 11 to be analyzed having certain flexibility or elasticity, better coupling of excitation light energy is obtained if the matrix 30 is slightly pressed into this medium, as illustrated FIG. 7. In this figure, the example is taken of a matrix of the type shown FIG. 3, but the same result is valid for any other matrix according to the present invention.

With respect to living tissues, this is attributed to the fact that blood, responsible for absorption, is then locally expelled by the pressure exerted on the matrix, as indicated by the arrows 55, 57 in FIG. 7. The air (between the surface 22 of the matrix 30 and the surface 11' of the tissue 11) is also expelled, also making it possible to achieve better coupling by minimizing the tissue/air interface. The pressure exerted on the matrix 30 therefore provides better coupling of incident radiation with the medium and better coupling of the signal emitted by the medium with the collection device according to the invention.

More generally, if the examined medium contains a fluid, a pressure applied to the coupling device of the invention allows this fluid to be repelled or evacuated outside the examined regions, which contributes towards a better measured signal.

Figure 8A:
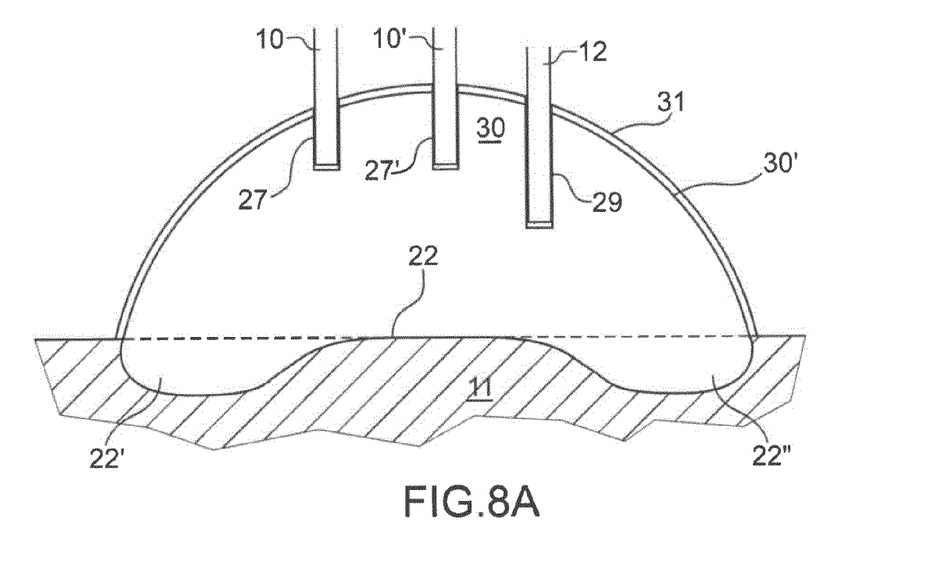
FIGS. 8A-8D are examples of another embodiment of the invention, each with a matrix provided with one or more protuberances.

Also, to ensure good coupling between a coupling device according to the invention and the examined medium, it is possible to provide a bearing surface 22 having one or more projections or protuberances 22', 22" which may have a substantially rounded or convex shape, with no sharp edges as illustrated FIG. 8A.

The device according to the invention then comprises a contact surface 22 with the medium 11 to be examined, a surface which has at least one non-zero radius of curvature in a plane perpendicular to the surface of this medium.

Said projection or protuberance is a portion or region of material which extends beyond the main bearing surface 22, in the direction of the matter to be analyzed. While the main bearing surface 22 is in contact with surface 11 of the matter to be analyzed, the protuberance enters more deeply into this matter. This forms a region of matter for the matrix 20, a region which will be surrounded by matter to be analyzed, as will be understood from FIG. 8A which illustrates the matrix with two protuberances 22', 22" pressed into the matter 11.

Figure 8B:
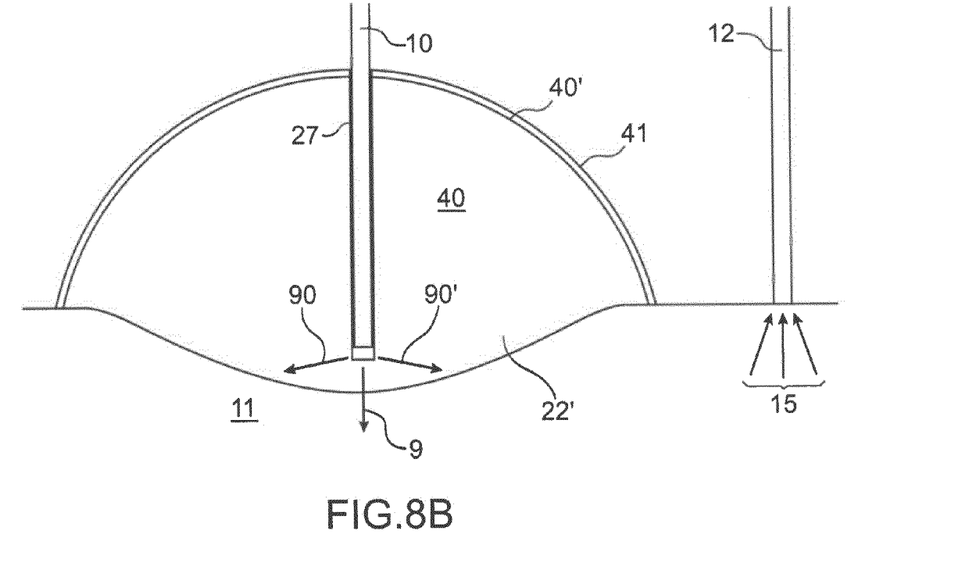

FIG. 8B shows a variant of this embodiment. This time, the example is taken of a system of the type shown FIG. 6A, with an excitation fibre in the matrix. The end of the fibre 10 is placed in a protuberance 22', the entry of the photons into the medium to be analyzed is therefore much more efficient since photons or radiation 90, 90' which could have escaped e.g. laterally without giving rise to any interaction with the matter 11, will on the contrary come to meet the matter and thereby reinforce and impart greater efficacy to the excitation signal.

Figure 8C:
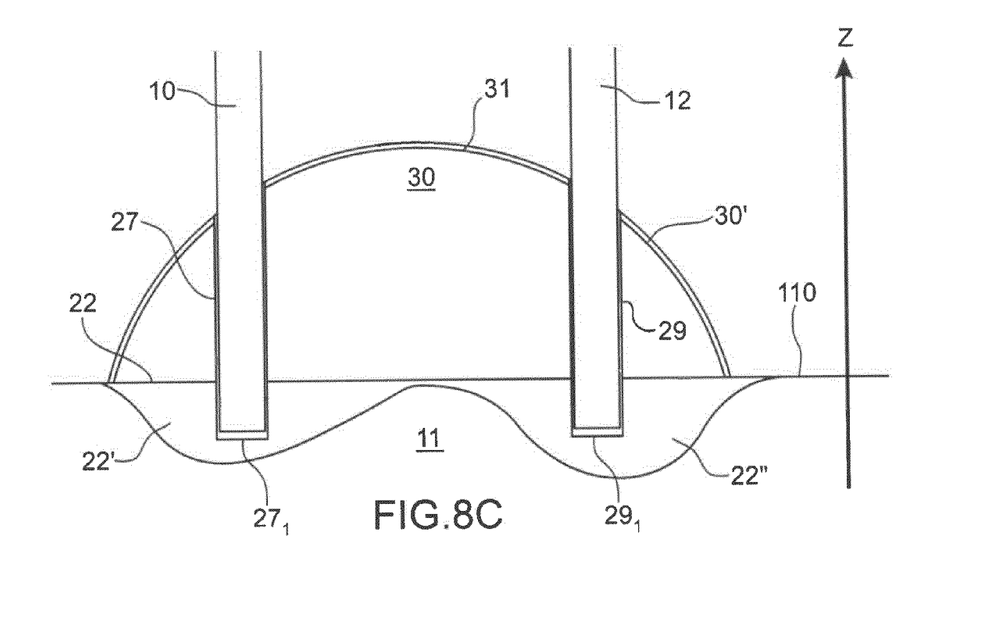
Figure 8D:
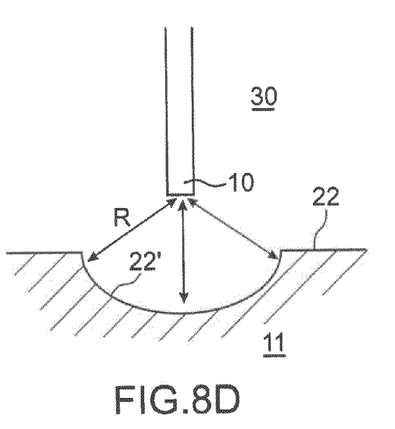

Preferably, and as illustrated FIG. 8D, the end of the excitation fibre 10 is placed in the centre of the curvature of the protuberance 22', the latter having a substantially constant radius of curvature. With this arrangement, it is possible to obtain homogeneous excitation over the entire surface of the tissue in contact with the protuberance.

In this example, the signal collection fibre is located next to the matrix 40.

Signal collection is also reinforced if the fibre 12 is also placed in the matrix (as in FIG. 3) and if its end is also placed in a protuberance 22": this gives the structure shown FIG. 8C. In this figure, as in FIG. 8B, it can be seen that the end $27_1, 27_2$ of each cavity 27, 29 is arranged along axis z under the surface 110 which delimits the medium 11 to be examined either side of the device.

In all cases, the protuberances 22', 22" can be in a material identical to the constituent material of the matrix 20.

In all cases, between the surface 22 and the surface of the matter to examined, it is possible to add a liquid preferably having a refractive index close to that of the medium or material. (Viscous for example, e.g. intralipid for further improved coupling). This liquid is preferably transparent and with negligible diffusion. Without this liquid, the application of a pressure to expel the air between the surface 22 of the matrix 20 and the surface 110 of the material to be examined 11 is itself sufficient to allow good coupling to be achieved.

The invention claimed is:

1. A diffuse optical imaging device to image a medium, comprising:
   a radiation source to form incident radiation on the medium, at least at a first wavelength;
   a device to detect a diffused or fluorescence signal emanating from the medium;
   a coupling device including:
      a mass comprising a bearing surface to be applied against a surface of the medium,
      an absorbent layer at least partly covering the mass of the diffusing material,
      at least one collection optical fibre to collect a signal emanating from the medium, and to convey the signal collected towards the detection device, and
      at least one excitation optical fibre to bring the incident radiation onto the medium to be examined, optical fibre:
         either having one end arranged permanently in a diffusing material,
         or the coupling device comprising at least one housing to receive said optical fibre, this housing being provided in a mass of the diffusing material,
      an end of the collection optical fibre or a bottom of the housing to receive the collection optical fibre being located at a distance (h) from the bearing surface shorter than a distance (H) from the bearing surface at which an end of the excitation optical fibre or the bottom of the housing to receive the excitation optical fibre is located,
      said mass of the coupling device being the diffusing material for a wavelength guided by at least one of the optical fibres, the diffusing material capturing photons not directed towards the end of the collection optical fibre and redirecting the captured photons to the end of the collection optical fibre.

2. The device according to claim 1, wherein the diffusing material has a reduced diffusion coefficient higher than 0.1 $cm^{-1}$ and less than 700 $cm^{-1}$.

3. The device according to claim 1, wherein the diffusing material has an absorption coefficient higher than 0.01 $cm^{-1}$ and less than 1 $cm^{-1}$.

4. The device according to claim 1, wherein a spot of at least one incident beam, on the bearing surface intended to be in contact with the medium to be examined, has a surface area $S_t$ of between 1 mm$^2$ and fifty cm$^2$.

5. The device according to claim 1, wherein the bearing surface further comprising one or more convex protuberances with no sharp edges.

6. The device according to claim 5, comprising at least one of:
at least one housing whose bottom is located substantially in or at the protuberance; and
at least one fibre whose end is arranged in or at said protuberance.

7. The device according to claim 1, wherein said radiation source is a pulsed, continuous-time or amplitude-modulated source.

8. An examination method of optical tomography type to examine part of a medium, wherein at least one device is used according to claim 1, and wherein:
the coupling device is applied against this medium,
the medium is illuminated or subjected to optical excitation using the radiation source to form incident radiation on the medium, then to cause this incident radiation to enter the medium, and
an optical signal emanating from the medium is collected by the at least one collection optical fibre.

9. The method according to claim 8, wherein a fluid is applied between the bearing surface of the diffusing material of the coupling device and the surface of the medium.

10. The method according to claim 8, wherein a pressure is applied to the coupling device when it is in position against the medium, to cause fluid contained in this medium to flow out of part of this medium towards a region located on a periphery of the coupling device.

11. A diffuse optical imaging device to image a medium, comprising:
a matrix or mass of material comprising a bearing surface with one or more convex protuberances and no sharp edges to be applied against a surface of the medium, the one or more protuberances extending into the medium; and
at least one optical fibre of which one end is arranged permanently in a diffusing material and/or at least one housing provided in the matrix or mass to receive the end of the optical fibre, said matrix or mass of material being the diffusing material for a wavelength guided by said optical fibre, and said matrix or mass of material separating the optical fibre from the medium by a predetermined amount,
wherein one of said protuberances has a substantially constant radius of curvature, said device further comprising an excitation fibre whose end is placed in a centre of said curvature.

12. The device according to claim 11, comprising at least one of:
at least one housing whose bottom is located substantially in or at the protuberances; and
at least one fibre whose end is arranged in or at said protuberances.

13. An examination method of optical tomography type to examine part of a medium, wherein at least one device is used according to claim 11 and wherein:
the coupling device is applied against this medium,
the excitation fibre in the mass whose end is placed in a centre of a curvature of the protuberance obtains homogeneous excitation over an entire surface of the medium in contact with the protuberance forming a radiation source,
an optical signal emanating from the medium is collected by at least one collection optical fibre.

14. An examination method of optical tomography type to examine part of a medium, wherein at least one device is used according to claim 11 and wherein:
the coupling device is applied against this medium,
the medium is illuminated or subjected to optical excitation using a radiation source to form incident radiation on the medium,
the mass comprises a detection fibre whose end is placed in a centre of a curvature of one of the protuberances to collect a homogeneous optical signal emanating from the medium.

15. A diffuse optical imaging device to image a medium, comprising:
a radiation source to form incident radiation on the medium, at least at a first wavelength;
a device to detect a diffused or fluorescence signal emanating from the medium;
a coupling device including:
a mass comprising a bearing surface to be applied against a surface of the medium,
at least one collection optical fibre to collect a signal emanating from the medium, and to convey the signal collected towards the detection device, and
at least one excitation optical fibre to bring the incident radiation onto the medium to be examined, optical fibre:
either having one end arranged permanently in a diffusing material,
or the coupling device comprising at least one housing to receive said optical fibre, this housing being provided in a mass of the diffusing material,
an end of the collection optical fibre or a bottom of the housing to receive the collection optical fibre being located at a distance (h) from the bearing surface shorter than a distance (H) from the bearing surface at which an end of the excitation optical fibre or the bottom of the housing to receive the excitation optical fibre is located,
said mass of the coupling device being the diffusing material for a wavelength guided by at least one of the optical fibres, and
an absorbent layer at least partly covering the mass of the diffusing material.

16. The device according to claim 15, wherein the diffusing material has a reduced diffusion coefficient higher than 0.1 cm$^{-1}$ and less than 700 cm$^{-1}$.

17. The device according to claim 15, wherein the diffusing material has an absorption coefficient higher than 0.01 cn$^{-1}$ and less than 1 cm$^{-1}$.

18. The device according to claim 15, wherein a spot of at least one incident beam, on the bearing surface intended to be in contact with the medium to be examined, has a surface area $S_t$ of between 1 mm$^2$ and fifty cm$^2$.

19. An examination method of optical tomography type to examine part of a medium, wherein at least one device is used according to claim 15, and wherein:
the coupling device is applied against this medium,
the medium is illuminated or subjected to optical excitation using the radiation source to form incident radiation on the medium, then to cause this incident radiation to enter the medium, and
an optical signal emanating from the medium is collected by the at least one collection optical fibre.

* * * * *